(12) United States Patent
Pacioretty et al.

(10) Patent No.: US 8,029,831 B2
(45) Date of Patent: Oct. 4, 2011

(54) FORMULATIONS CONTAINING THYMOQUINONE FOR URINARY HEALTH

(75) Inventors: Linda M. Pacioretty, Brooktondale, NY (US); John G. Babish, Brooktondale, NY (US)

(73) Assignee: Bionexus, Ltd., Ithaca, NY (US)

( * ) Notice: Subject to any disclaimer, the term of this patent is extended or adjusted under 35 U.S.C. 154(b) by 434 days.

(21) Appl. No.: 12/220,811

(22) Filed: Jul. 29, 2008

(65) Prior Publication Data

US 2010/0028468 A1 Feb. 4, 2010

(51) Int. Cl.
*A61K 36/04* (2006.01)
*A61K 36/00* (2006.01)

(52) U.S. Cl. ........................ 424/732; 424/725

(58) Field of Classification Search ................... None
See application file for complete search history.

(56) References Cited

U.S. PATENT DOCUMENTS 6,231,866 B1* 5/2001 Mann ............................ 424/732
2002/0168429 A1* 11/2002 Mann ............................ 424/732

OTHER PUBLICATIONS

Roy et al. African J. Tradtional Complemenary Alternative Med. 2006. vol. 3, No. 2, pp. 1-7.*
Wang et al. Trends in Food Sci Tech. 2006, pp. 300-312.*
Roy et al. Bangleadesh Renal Journal 1992. vol. 11, No. 1, pp. 13-17, EMBASE Abstract enclosed.*

* cited by examiner

*Primary Examiner* — Christopher R. Tate

(57) ABSTRACT

A novel dietary supplement or therapeutic composition is provided that serves to treat lower urinary tract disorders or to support normal urinary tract function in animals. The supplement comprises a thymoquinone formulation and at least one member of the group consisting of cranberry fruit, cranberry extract, cranberry juice and a pharmaceutical grade methionine.

4 Claims, 2 Drawing Sheets

US 8,029,831 B2

FORMULATIONS CONTAINING THYMOQUINONE FOR URINARY HEALTH

CROSS-REFERENCE TO RELATED APPLICATIONS

None

BACKGROUND OF THE INVENTION

1. Field of the Invention

The present invention relates generally to formulations that can be taken as dietary supplements, and more particularly, to a specific thymoquinone containing extract of Nigella sativa seed and cranberry fruit extract or methionine to address general physiological stress as well as inflammation and microbial infections of the female urinary tract.

2. Description of the Related Art

Reoccurring cystitis or urologic syndrome generally manifests a combination of symptoms including irrative voiding, hematuria or inappropriate urination. Often seen in females of nearly all species, the most common form is termed idiopathic lower urinary tract disease or idiopathic cystitis. Other forms of urologic syndrome include urolithiasis, urinary tract infections and, least common, anatomic deficits (FIG. 1).

Research indicates that nitric oxide (NO) plays an important role in the pathogenesis of cyclophosphamide-induced cystitis in rats, and some factors may be released in cyclophosphamide-treated rat plasma that stimulate iNOS (inducible nitric oxide synthase) expression in primary culture of rat bladder smooth muscle cells [Xu X, Cubeddu L X, Malave A. Expression of inducible nitric oxide synthase in primary culture of rat bladder smooth muscle cells by plasma from cyclophosphamide-treated rats. *Eur J Pharmacol*. Mar. 23, 2001; 416(1-2):1-9]. Alterations in NO levels have been demonstrated in some humans with interstitial cystitis as well as in chemically induced animal models of cystitis [Koskela L R, Thiel T, Ehren I, De Verdier P J, Wiklund N P. Localization and expression of inducible nitric oxide synthase in biopsies from patients with interstitial cystitis. *J Urol*. August 2008; 180(2):737-741. Wilkinson D R, Erickson A D. Urinary and Serologic Markers for Interstitial Cystitis: An Update. *Curr Urol Rep*. September 2006; 7(5):414-422]. A significant increase in baseline NO production in cats with feline interstitial cystitis compared with that in healthy cats has been found in smooth muscle and mucosal strips. It has been shown that the barrier property of the urothelial surface is disrupted in feline interstitial cystitis and iNOS mediated increase in NO alters barrier function in other types of epithelium. Additionally, iNOS dependent NO production may have a role in epithelial barrier dysfunction in feline interstitial cystitis [Birder L A, Wolf-Johnston A, Buffington C A, Roppolo J R, de Groat W C, Kanai A J. Altered inducible nitric oxide synthase expression and nitric oxide production in the bladder of cats with feline interstitial cystitis. *J Urol*. February 2005; 173(2):625-629]. Therefore, inhibitors of iNOS may be useful agents in the treatment of interstitial cystitis.

There appears to be no single, primary causative agent associated with idiopathic cystitis. Among the risk factors identified, stress and a urinary pH greater than 7.0 are most frequently reported. While bacterial infection seems to play a primary role in the disease, several research groups have proposed that viral infections may have a predisposing influence. Low fuid intake is also considered a significant risk factor for recurrent idiopathic cystitis.

Oral medications that may improve the signs and symptoms of interstitial cystitis include ibuprofen and other non-steroidal pain medications to relieve discomfort. Antibiotics, steroids, diet change, and/or increased water intake are the commonly prescribed treatments. But treatment of idiopathic cystitis with presently available formulations has drawbacks. For example, reduction of stress is considered critical to terminating the cycle of recurrence. Treatment with amitriptyline, one of the early tricyclic antidepressants, has been reported to be highly effective in reducing the frequency of episodes in severe recurrent cases of idiopathic cystitis. However, potential side-effects of amitriptyline include sedation, hypotension, and weight gain.

Moreover, episodes of idiopathic cystitis tend to be self-limiting and resolve within ten days regardless of the treatment, but if the risk factors for idiopathic cystitis are not addressed, the likelihood of recurrence is high. And a frequent complication in active untreated cystitis includes increased risk of infection, often leading to inflammation and painful urination.

Research suggests that acidifying the urine may be effective in the management of recurrent idiopathis cystitis. Ingestion of cranberry fruit juice and methionine are speculated to help provide such acidification. One double-blind, placebo-controlled study of 153 elderly women indicated that the consumption of 300 mL of commercially available standard cranberry juice reduced the odds of bacteriuria by forty-two percent [Avorn et al., *Reduction of bacteriuria and pyuria after ingestion of cranberry juice*, 271 JAMA 751-754 (1994)]. Other studies suggest that cranberry juice may be more effective in treating than in preventing bacteriuria and urinary tract infections [Fleet, J. C. *New support for a folk remedy: cranberry juice reduces bacteriuria and pyuria in elderly women*, 52 NUTR. REC. 168-170 (1994)]. However, it is unclear whether the positive results obtained with cranberry fruit juice are due to some ingredient of cranberries, such as quinic acid, which is thought to have an antimicrobial role, or whether any observed positive results are due simply to the consumption of additional fluids.

While ingestion of cranberry fruit juice is thought to be useful for alleviating urinary cystitis, the efficacy of a cranberry fruit extract for the same application has not been demonstrated. Publications relating to the efficacy of cranberry fruit and cystitis report on the use of cranberry fruit juice and not on cranberry fruit extracts. Moreover, any positive clinical results obtained with cranberry fruit juice may simply be due to the consumption of additional fluids, a practice known to reduce the risk of urinary tract infections.

Today, cranberry fruit extract is widely available in America and European countries as a dietary supplement in the form of tablets, capsules or gel caps. Examples of available cranberry fruit extract products include the following trade designations, with the milligrams of extract in a dose indicated parenthetically if known: HealthCare Cranberry Fruit (475 mg capsules, 2 to 4 capsules three times daily) and YourLife Cranberry (300 mg caplets, 2 caplets three times daily).

However, while the historical and clinical use of cranberry fruit juice may indicate that cranberries are useful for treating urinary tract infections, cranberry fruit extract has not been optimally formulated into a dietary supplement that can effectively relieve all the symptoms of recurrent idiopathic cystitis [Jepson R G, Craig J C. Cranberries for preventing urinary tract infections. *Cochrane Database Syst Rev.* 2008(1): CD001321].

An ideal formulation for the reduction of risk factors associated with cystitis would (i) decrease urinary pH, (ii) reduce physiological stress, (iii) reduce pain, and (iv) decrease the inflammatory response by inhibiting iNOS-mediated NO production. Such a formulation should therefore enhance potential acidification properties offered by cranberry fruit and address the additional risk factors of physiological stress, inflammation and infection. It should be inexpensively manufactured and comply with all governmental regulations. While it may provide one or two of these features, cranberry juice and cranberry extracts cannot provide all of these desirable features. Therefore, a formulation containing cranberry juice, cranberry extracts or any of its active ingredients with other beneficial ingredients would be an improvement over those presently commercially available.

Methionine is an amino acid that may help acidify urine and doses are available commercially in amounts ranging from 200 to 600 mg. Methionine has been used clinically to acidify the urine. Doses of 1500 to 3000 mg/day in humans reduced the mean pH values of the urine of 19 subjects from 7.5 to 5.5 [Jarrar, K., R. H. et al., Struvite stones: long term follow-up under metaphylaxis, 30 ANN UROL. (Paris) 112-117 (1996)].

*Nigella sativa*, commonly known as black seed or black curcumin, is traditionally used in the Indian subcontinent, Arabian countries, and Europe for culinary and medicinal purposes as a natural remedy for a number of illnesses and conditions that include asthma, hypertension, diabetes, inflammation, cough, bronchitis, headache, eczema, fever, dizziness and influenza. Much of the biological activity of the seeds has been shown to be due to thymoquinone, the major component of the essential oil, but which is also present in the fixed oil.

The seeds of *N. sativa* as well as thymoquinone are characterized by a very low degree of toxicity. Administration of either the seed extract or its oil has been shown not to induce significant adverse effects on liver or kidney functions even at extremely high doses [Ali B H, Blunden G. 2003. Pharmacological and toxicological properties of *Nigella sativa*. *Phytother Res* 17: 299-305]. Thus, thymoquinone possesses the necessary safety factor for commercialization in the dietary supplement market.

As seen in Table 1, thymoquinone content of the essential (volatile) oil fraction is roughly 27-57 percent. The essential oil fraction, however, constitutes only one percent of the seed oils. Thus, thymoquinone comprises only about 0.3 to 0.6% of the fixed oil fraction, the most common commercially available product of *N. sativa*.

Traditional solvent extraction is time-consuming, requires multiple steps, and consumes large amounts of organic solvents. The amount and the price of organic solvent directly influences the total cost of producing an acceptable extract or product. Moreover, when the final product is used as a food ingredient, it is absolutely necessary to remove all potentially toxic solvents.

TABLE 1

Thymoquinone content of various oil fractions of *N. sativa* seeds

| FRACTION | COMPONENT | CONTENT [% w/w] |
|---|---|---|
| Seeds | Fixed oils. | 36 |
| Fixed oil (cold pressed) | Fatty acids, protein, thiamin, ribovflavin, pyridoxine, niacin, folic acid, and calcium. | 58 |
| Essential fatty acids in fixed oil | Myristic acid (C14) | 0.5 |
|  | Palmitic acid (C16) | 13.7 |
|  | Palmitoleic acid (C16 w-9) | 0.1 |
|  | Stearic acid (C18) | 2.6 |
|  | Linoleic acid (C18 w-6) | 57.9 |
|  | Linolenic acid (C18 w-3) | 0.2 |
|  | Arachidic acid (C20 | 1.3 |
|  | Essential oil | 0.5-1.5 |
| Essential oil (volatile oil) | Thymoquinone | 27-57 |
|  | p-Cymene | 7.1-15.5 |
|  | Carvacrol | 5.8-11.6 |
|  | trans-Anethole | 0.25-2.3 |
|  | p-terpineol | 2.0-6.6 |
|  | longifoline | 1.0-8.0 |

Supercritical fluid extraction (SFE) has already proven itself as an attractive technique for selectively removing compounds from complex food matrices. Specifically SFE offers the possibility of mild extraction conditions combined with low energy requirements for solvent recovery. The high selectivity of the extraction process and the reduced potential for oxidation of the extracted materials make this technique especially suitable for extractive isolation of natural products. The lone drawback to SFE is the high capital cost of the extraction set-up.

A novel, supercritical $CO_2$ extract of *N. sativa* has is described that contains 2.0 to 6.0% (w/w) thymoquinone, an amount between that of the fixed and essential oils, and exhibits anti-inflammatory activity in excess of its thymoquinone content alone. This novel thymoquinone composition may also be obtained commercially from Garden State Nutritionals, 8 Henderson Drive, West Caldwell N.J.

However, thymoquinone has not been optimally formulated into compositions that can reduce all of risk factors associated with cystitis and thereby: (i) decrease urinary pH, (ii) reduce physiological stress, (iii) reduce pain, and (iv) decrease the inflammatory response. Therefore, a formulation containing thymoquinone and cranberry juice, cranberry extracts or any of the active ingredients of cranberry fruit, with the other beneficial ingredients contemplated by the present invention, would be an improvement over formulations that are presently commercially available.

SUMMARY OF THE INVENTION

The present invention provides a composition, which may be taken as a dietary supplement, that comprises a SFE of thymoquinone containing 2.0 to 6.0% (w/w) thymoquinone and at least one member selected from the group comprising cranberry fruit extract and methionine. The present supplement (i) reduces the pH of the urine, (ii) provides antimicrobial activity, (iii) addresses inflammation and pain through the inhibition of iNOS mediated NO biosynthesis and (iv) decreases physiological stress. Working together, the components are designed to reduce the frequency of recurrent idiopathic cystitis and to normalize urinary tract function.

The present invention also provides a method of dietary supplementation in animals comprising administering to an animal synergistically effective amounts thymoquinone and at least one member of the group consisting of cranberry extract and methionine. This method can be used to enhance the urinary health of the animal.

The present invention further provides a method of treating recurrent idiopathic cystitis in an animal comprising administering to an animal suffering symptoms of recurrent idiopathic cystitis a synergistically effective amount of thymoquinone and at least one member selected from the group consisting of a cranberry extract and methionine, and continuing the administration of the composition until the symptoms are reduced.

DETAILED DESCRIPTION OF THE INVENTION

Figure 1:
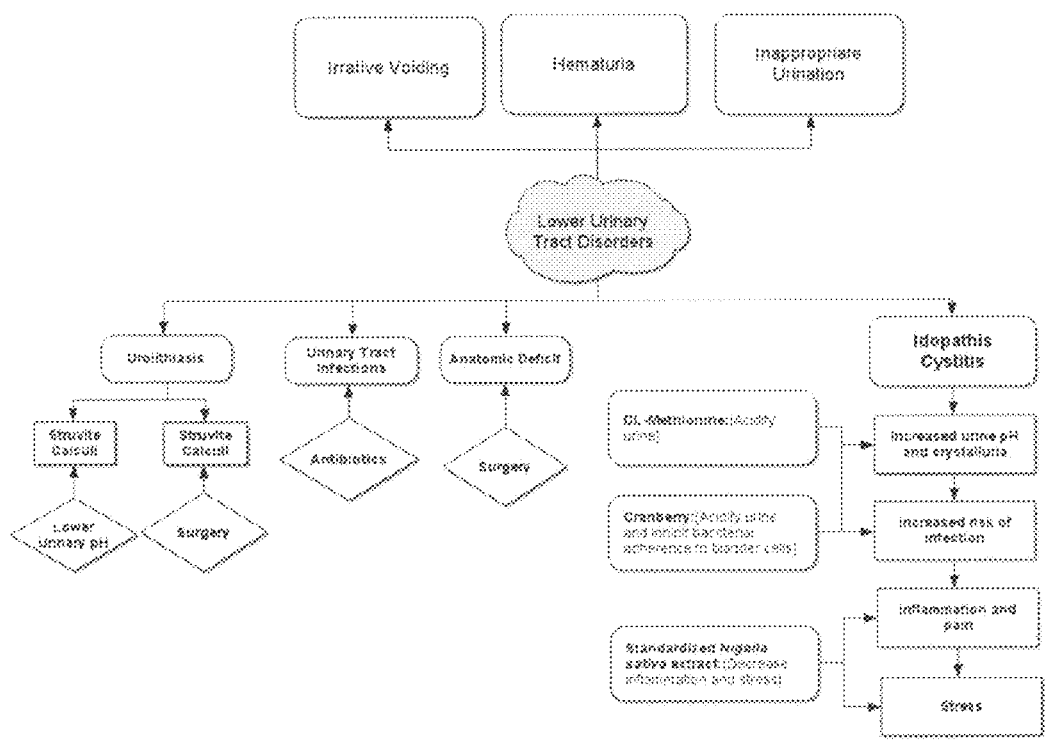
FIG. 1 provides a schematic of the breakdown of lower urinary tract disorders and the risk factors associated with idiopathic cystitis.

The compositions of the invention include a thymoquinone formulation containing 2.0 to 6.0% (w/w) thymoquinone, used for its anti-inflammatory and stress-reducing properties, and a at least one member selected from the group consisting of cranberry fruit juice or extract and methionine. The resulting composition can be used as a dietary supplement to address the risk factors associated with reoccurring urinary cystitis without introducing any harmful side effects. Thus, the present composition is useful as a therapeutic aid for the treatment of recurrent idiopathic cystitis or urinary tract infection and for maintaining the health of the urinary system.

The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of recombinant DNA technology include Sambrook et al., Molecular Cloning: A Laboratory Manual, 2nd Ed., Cold Spring Harbor Laboratory Press, New York (1989); Kaufman et al., Eds., Handbook of Molecular and Cellular Methods in Biology in Medicine, CRC Press, Boca Raton (1995); McPherson, Ed., Directed Mutagenesis: A Practical Approach, IRL Press, Oxford (1991). Standard reference works setting forth general definitions of medical terms and the general principles of pharmacology, respectively, include Stedman's Medical Dictionary [26$^{th}$ edition] and Goodman and Gilman's The Pharmacological Basis of Therapeutics, 11th Ed., McGraw Hill Companies Inc., New York (2006).

In the specification and the appended claims, the singular forms include plural referents unless the context clearly dictates otherwise. As used in this specification, the singular forms "a," "an" and "the" specifically also encompass the plural forms of the terms to which they refer, unless the content clearly dictates otherwise. Additionally, as used herein, unless specifically indicated otherwise, the word "or" is used in the "inclusive" sense of "and/or" and not the "exclusive" sense of "either/or." The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable that is inherently discrete, the variable can be equal to any integer value of the numerical range, including the end-points of the range. Similarly, for a variable that is inherently continuous, the variable can be equal to any real value of the numerical range, including the end-points of the range. As an example, a variable that is described as having values between 0 and 2 can be 0, 1 or 2 for variables that are inherently discrete, and can be 0.0, 0.1, 0.01, 0.001, or any other real value for variables that are inherently continuous.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or compounds, but may also include additional features or compounds.

Reference is made hereinafter in detail to specific embodiments of the invention. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail, in order not to unnecessarily obscure the present invention.

Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The term "treat" and its verbal variants refer to palliation or amelioration of an undesirable physiological state. Thus, for example, where the physiological state is poor glucose tolerance, "treatment" refers to improving the glucose tolerance of a treated subject. As another example, where the physiological state is obesity, the term "treatment" refers to reducing the body fat mass, improving the body mass or improving the body fat ratio of a subject. Treatment of diabetes means improvement of blood glucose control. Treatment of inflammatory diseases means reducing the inflammatory response either systemically or locally within the body. Treatment of osteoporosis means an increase in the density of bone mineralization or a favorable change in metabolic or systemic markers of bone mineralization. The person skilled in the art will recognize that treatment may, but need not always, include remission or cure.

The term "prevent" and its variants refer to prophylaxis against a particular undesirable physiological condition. The prophylaxis may be partial or complete. Partial prophylaxis may result in the delayed onset of a physiological condition.

The person skilled in the art will recognize the desirability of delaying onset of a physiological condition, and will know to administer the compositions of the invention to subjects who are at risk for certain physiological conditions in order to delay the onset of those conditions. For example, the person skilled in the art will recognize that obese subjects are at elevated risk for coronary artery disease. Thus, the person skilled in the art will administer compositions of the invention in order to increase insulin sensitivity in an obese, whereby the onset of diabetes mellitus or dyslipemia may be prevented entirely or delayed.

In regard to improvement of urinary health, then, a subject may be an animal or human who has been diagnosed with cystitis or bladder infection or an animal or human, who is determined to be at risk for cystitis or bladder infection. The ordinary clinician will be able to diagnose cystitis or bladder infection and, via analysis of a subject's health history, determine whether the subject is at risk for cystitis or bladder infection.

The methods of the present invention are intended for use with any subject that may experience the benefits of the methods of the invention. Thus, in accordance with the invention, "subjects" include humans as well as non-human subject, particularly domesticated animals. It will be understood that the subject to which a compound of the invention is administered need not suffer from a specific traumatic state. Indeed, the compounds of the invention may be administered prophylactically, prior to any development of symptoms. The term "therapeutic," "therapeutically," and permutations of these terms are used to encompass therapeutic, palliative as well as prophylactic uses.

As used herein, the term "solvent" refers to a liquid of aqueous or organic nature possessing the necessary characteristics to extract solid material from the N. sativa seed product. Examples of solvents would include, but not limited to, water, steam, superheated water, methanol, ethanol, hexane, chloroform, liquid $CO_2$, liquid $N_2$, propane, or any combinations of such materials.

As used herein, the term "$CO_2$ extract" refers to the solid material resulting from exposing a N. sativa seed product to a liquid or supercritical $CO_2$ preparation followed by subsequent removal of the $CO_2$.

As used herein, "decreased secretion," means to decrease by at least 3%, the rate of secretion or amount of secretion of the referent compound. The invention further provides a method of decreasing myocyte concentrations of inflammatory mediators in a subject, comprising administering to the subject an amount of the composition sufficient to decrease NO secretion from bladder myocytes in the subject. In general, a decrease in bladder myocytes NO will result in improved urinary bladder health and decreased secretion of pro-inflammatory mediators in the urinary bladder.

In some aspects the compositions further comprise a pharmaceutically acceptable excipient where the pharmaceutically acceptable excipient is selected from the group consisting of coatings, isotonic and absorption delaying agents, binders, adhesives, lubricants, disintergrants, coloring agents, flavoring agents, sweetening agents, absorbants, detergents, and emulsifying agents. In yet further aspects, the composition additionally comprises one or more members selected from the group consisting of antioxidants, vitamins, minerals, proteins, fats, and carbohydrates.

The term "therapeutically effective amount" is used to denote treatments at dosages effective to achieve the therapeutic result sought. Furthermore, one of skill will appreciate that the therapeutically effective amount of the compound of the invention may be lowered or increased by fine-tuning and/or by administering more than one compound of the invention, or by administering a compound of the invention with another compound. See, for example, Meiner, C. L., "Clinical Trials: Design, Conduct, and Analysis," Monographs in Epidemiology and Biostatistics, Vol. 8 Oxford University Press, USA (1986). The invention therefore provides a method to tailor the administration/treatment to the particular exigencies specific to a given mammal. As illustrated in the following examples, therapeutically effective amounts may be easily determined, for example, empirically by starting at relatively low amounts and by step-wise increments with concurrent evaluation of beneficial effect.

The term "pharmaceutically acceptable" is used in the sense of being compatible with the other ingredients of the compositions and not deleterious to the recipient thereof.

As used herein, "compounds" may be identified either by their chemical structure, chemical name, or common name. When the chemical structure and chemical or common name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated or identified compounds including the stereoisomerically pure form (e.g, geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated or identified compounds. The compounds described also encompass isotopically labeled compounds where one or more atoms have an atomic mass different from the atomic mass conventionally found in nature. Examples of isotopes that may be incorporated into the compounds of the invention include, but are not limited to, $^2H$, $^3H$, $^{13}C$, $^{14}C$, $^{15}N$, $^{18}O$, $^{17}O$, etc. Compounds may exist in unsolvated forms as well as solvated forms, including hydrated forms and as N-oxides. In general, compounds may be hydrated, solvated or N-oxides. Certain compounds may exist in multiple crystalline or amorphous forms. Also contemplated within the scope of the invention are congeners, analogs, hydrolysis products, metabolites and precursor or prodrugs of the compound. In general, all physical forms are equivalent for the uses contemplated herein and are intended to be within the scope of the present invention.

The compounds according to the invention are optionally formulated in a pharmaceutically acceptable vehicle with any of the well-known pharmaceutically acceptable carriers, including diluents and excipients (see Remington's Pharmaceutical Sciences, 18th Ed., Gennaro, Mack Publishing Co., Easton, Pa. 1990 and Remington: The Science and Practice of Pharmacy, Lippincott, Williams & Wilkins, 1995). While the type of pharmaceutically acceptable carrier/vehicle employed in generating the compositions of the invention will vary depending upon the mode of administration of the composition to a mammal, generally pharmaceutically acceptable carriers are physiologically inert and non-toxic. Formulations of compositions according to the invention may contain more than one type of compound of the invention), as well any other pharmacologically active ingredient useful for the treatment of the symptom/condition being treated.

The compounds of the present invention may be provided in a pharmaceutically acceptable vehicle using formulation methods known to those of ordinary skill in the art. The compositions of the invention can be administered by standard routes. The compositions of the invention include those suitable for oral, inhalation, rectal, ophthalmic (including intravitreal or intracameral), nasal, topical (including buccal and sublingual), vaginal, or parenteral (including subcutaneous, intramuscular, intravenous, intradermal, and intratracheal). In addition, polymers may be added according to standard methodologies in the art for sustained release of a given compound.

It is contemplated within the scope of the invention that compositions used to treat a disease or condition will use a pharmaceutical grade compound and that the composition will further comprise a pharmaceutically acceptable carrier. It is further contemplated that these compositions of the invention may be prepared in unit dosage forms appropriate to both the route of administration and the disease and patient to be treated. The compositions may conveniently be presented in dosage unit form be prepared by any of the methods well known in the art of pharmacy. All methods include the step of bringing the active ingredient into association with the vehicle that constitutes one or more auxiliary constituents. In general, the compositions are prepared by uniformly and intimately bringing the active ingredient into association with a liquid vehicle or a finely divided solid vehicle or both, and then, if necessary, shaping the product into the desired composition.

The term "dosage unit" is understood to mean a unitary, i.e. a single dose which is capable of being administered to a patient, and which may be readily handled and packed, remaining as a physically and chemically stable unit dose comprising either the active ingredient as such or a mixture of it with solid or liquid pharmaceutical vehicle materials.

Compositions suitable for oral administration may be in the form of discrete units as capsules, sachets, tablets, soft gels or lozenges, each containing a predetermined amount of the active ingredient; in the form of a powder or granules; in the form of a solution or a suspension in an aqueous liquid or non-aqueous liquid, such as ethanol or glycerol; or in the form of an oil-in-water emulsion or a water-in-oil emulsion. Such oils may be edible oils, such as e.g. cottonseed oil, sesame oil, coconut oil or peanut oil. Suitable dispersing or suspending agents for aqueous suspensions include synthetic or natural gums such as tragacanth, alginate, gum arabic, dextran, sodium carboxymethylcellulose, gelatin, methylcellulose and polyvinylpyrrolidone. The active ingredient may also be administered in the form of a bolus, electuary or paste.

In addition to the compositions described above, the compositions of the invention may also be formulated as a depot preparation. Such long-acting compositions may be administered by implantation (e.g. subcutaneously, intraabdominally, or intramuscularly) or by intramuscular injection. Thus, for example, the active ingredient may be formulated with suitable polymeric or hydrophobic materials (for example, as an emulsion in a pharmaceutically acceptable oil), or an ion exchange resin.

The compounds of this invention either alone or in combination with each other or other compounds generally will be administered in a convenient composition. The following representative composition examples are illustrative only and are not intended to limit the scope of the present invention. In the compositions that follow, "active ingredient" means a compound of this invention.

As used herein, "therapeutically effective time window" means the time interval wherein administration of the compounds of the invention to the subject in need thereof reduces or eliminates the deleterious effects or symptoms. In a preferred embodiment, the compound of the invention is administered proximate to the deleterious effects or symptoms.

Without limiting the invention to an extact mechanism, the cranberry fruit (*Vaccinium macrocarpon*) extract provides (i) acidification of urine, (ii) inhibition of bacterial adherence to bladder cells, and (iii) reduction of bacteriuria and pyuria. The extract employed can be obtained commercially, for example, from Freeman Industries, L.L.C. 100 Marbledale Road, Tuckahow, N.Y. 10707-3420 which provides a 5:1 extract of cranberry fruit that has been standardized to contain about 3.4% quinic acid. According to the present invention, the cranberry fruit can be provided as about a 2:1 to about a 10:1 extract which contains about 10% to about 0.5% quinic acid.

Methionine is an amino acid that may additionally or solely acidify urine and can be obtained commercially from such sources as Sigma (St. Louis, Mo.).

In addition to cranberry fruit extract or methionine, the present composition contains at least one additional complementary herbal extract. The additional herbal extract is a defined *Nigella sativa* extract containing thymoquinone.

*Nigella sativa* Linn. (family: *Ranunculacease*), commonly known as black seed or black curcumin, is an annual plant that has been traditionally used in the Indian subcontinent, Arabian countries, and Europe for culinary and medicinal purposes as a natural remedy for a number of illnesses and conditions that include asthma, hypertension, diabetes, inflammation, cough, bronchitis, headache, eczema, fever, dizziness and influenza. The seeds or its oil are used as a carminative, diuretic, lactoagogue, and vermifuge. They are also used in food as a spice and a condiment.

*N. sativa* seeds contain 36-38% fixed oils, proteins, alkaloids, saponin and 0.4-2.5% essential oil. The fixed oil is composed mainly of unsaturated fatty acids, including the unusual C20:2 arachidic and eiosadienoic acids. Major components of the essential oil include thymoquinone (27-57%), p-cymene (7.1-15.5%), carvacrol (5.8-11.6%), trans-anethole (0.25-2.3%) p-terpineol (2.0-6.6%) and longifoline (1.0-8.0%). Thymoquinone readily dimerizes to form dithymoquinone and as used herein, thymoquinone will also refer to the naturally occurring dimmer dithymoquinone.

Many studies have been conducted, particularly during the past two decades, on the effect of *N. sativa* seed on various body systems in vivo or in vitro. Among those physiological effects studied include antioxidant effects, anti-inflammatory and analgesic actions, anticarcinogenic activity, hypotensive effects, antidiabetic, antiulcer, antimicrobial and antiparasitic actions [Ali B H, Blunden G. 2003. Pharmacological and toxicological properties of *Nigella sativa*. Phytother Res 17: 299-305].

Preferably, a daily dose (mg/kg-day) of the present dietary supplement would be formulated to deliver per kg body weight of the mammal the following active ingredients within the suggested ranges: (a) about 1 to 5 mg/kg thymoquinone formulation containing 2.0 to 6.0% (w/w) thymoquinone; and (b) about 10 to 40 mg/kg cranberry fruit extract and/or (c) about 5 to 50 mg/kg methionine.

In addition to the thymoquinone formulation, cranberry fruit extract and methionine, the present dietary supplement may include various additives such as other vitamins and minerals, as well as inert ingredients such as talc and magnesium stearate that are standard excipients in the manufacture of tablets and capsules. Other ingredients to affect the manufacture of this formulation as a dietary bar or functional food would obviously include flavorings, sugars, modified starches, grain products as well as fats and oils.

The present composition can be provided in any convenient form. It can be provided as dietary supplement in capsule or tablet form. It can be formulated into a food or drink, and provided, for example, as a snack bar, a cereal, a drink, a gum, or in any other easily ingested form. It can also be provided as a cream or lotion for topical application. One trained in the art can readily formulate the present composition into any of these convenient forms for oral or topical administration.

The amount of other additives per unit serving are a matter of design and will depend upon the total number of unit servings of the nutritional supplement daily administered to the patient. The total amount of other ingredients will also depend, in part, upon the condition of the patient. Preferably, the amount of other ingredients will be a fraction or multiplier of the RDA or DRI amounts. For example, the nutritional supplement will comprise 50% RDI (Reference Daily Intake) of vitamins and minerals per unit dosage and the patient will consume two units per day.

Flavors, coloring agents, spices, nuts and the like can be incorporated into the product. Flavorings can be in the form of flavored extracts, volatile oils, chocolate flavorings (e.g., non-caffeinated cocoa or chocolate, chocolate substitutes such as carob), peanut butter flavoring, cookie crumbs, crisp rice, vanilla or any commercially available flavoring. Flavorings can be protected with mixed tocopherols. Examples of useful flavorings include but are not limited to pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, cherry oil, walnut oil, cinnamon oil, clove oil, or peppermint oil; peanut butter, chocolate flavoring, vanilla cookie crumb, butterscotch or toffee. In a preferred embodiment, the nutritional supplement contains berry or other fruit flavor. The food compositions may further be coated, for example with a yogurt coating if it is as a bar.

Emulsifiers may be added for stability of the final product. Examples of suitable emulsifiers include, but are not limited to, lecithin (e.g., from egg or soy), or mono- and di-glycerides. Other emulsifiers are readily apparent to the skilled artisan and selection of suitable emulsifier(s) will depend, in part, upon the formulation and final product.

Preservatives may also be added to the nutritional supplement to extend product shelf life. Preferably, preservatives such as potassium sorbate, sodium sorbate, potassium benzoate, sodium benzoate or calcium disodium EDTA are used.

In addition to the carbohydrates described above, the nutritional supplement can contain natural or artificial sweeteners, e.g., glucose, sucrose, fructose, saccharides, cyclamates, aspartamine, sucralose, aspartame, acesulfame K, or sorbitol.

Manufacture of the Preferred Embodiments—The nutritional supplements of the present invention may be formulated using any pharmaceutically acceptable forms of the vitamins, minerals and other nutrients discussed above, including their salts. They may be formulated into capsules, tablets, powders, suspensions, gels or liquids optionally comprising a physiologically acceptable carrier, such as but not limited to water, milk, juice, soda, starch, vegetable oils, salt solutions, hydroxymethyl cellulose, carbohydrate. In a preferred embodiment, the nutritional supplements may be formulated as powders, for example, for mixing with consumable liquids, such as milk, juice, sodas, water or consumable gels or syrups for mixing into other nutritional liquids or foods. The nutritional supplements of this invention may be formulated with other foods or liquids to provide pre-measured supplemental foods, such as single serving beverages or bars, for example.

In a particularly preferred embodiment, the nutritional supplement will be formulated into a nutritional beverage, a form that has consumer appeal, is easy to administer and incorporate into one's daily regimen, thus increasing the chances of patient compliance. To manufacture the beverage, the ingredients are dried and made readily soluble in water. For the manufacture of other foods or beverages, the ingredients comprising the nutritional supplement of this invention can be added to traditional formulations or they can be used to replace traditional ingredients. Those skilled in food formulating will be able to design appropriate foods or beverages with the objective of this invention in mind.

The nutritional supplement can be made in a variety of forms, such as puddings, confections, (i.e., candy), nutritional beverages, ice cream, frozen confections and novelties, or non-baked, extruded food products such as bars. The preferred form is a powder to add to a beverage or a non-baked extruded nutritional bar. In another embodiment, the ingredients can be separately assembled. For example, certain of the ingredients (e.g., the conjugated fatty acids or alcohols and thiol compounds) can be assembled into a tablet or capsule using known techniques for their manufacture. The remaining ingredients can be assembled into a powder or nutritional bar. For the manufacture of a food bar, the dry ingredients are added with the liquid ingredients in a mixer and mixed until the dough phase is reached; the dough is put into an extruder and extruded; the extruded dough is cut into appropriate lengths; and the product is cooled. The two assembled forms comprise the nutritional supplement and can be packaged together or separately, such as in the form of a kit, as described below. Further, they can be administered together or separately, as desired.

Use of Preferred Embodiments—The preferred embodiments contemplate treatment of urinary bladder related disorders. A pharmaceutically acceptable carrier may also be used in the present compositions and formulations. The recommended daily amounts of each ingredient, as described above, serve as a guideline for formulating the nutritional supplements of this invention. The actual amount of each ingredient per unit dosage will depend upon the number of units daily administered to the individual in need thereof. This is a matter of product design and is well within the skill of the nutritional supplement formulator.

The ingredients can be administered in a single formulation or they can be separately administered. For example, it may be desirable to administer the compounds in a form that masks their taste (e.g., capsule or pill form) rather than incorporating them into the nutritional composition itself (e.g., powder or bar). Thus, the invention also provides a pharmaceutical pack or kit comprising one or more containers filled with one or more of the ingredients of the nutritional compositions of the invention (e.g., nutritional supplement in the form of a powder and capsules containing thymoquinone and/or synephrine). Optionally associated with such container(s) can be a notice in the form prescribed by a government agency regulating the manufacture, use or sale of pharmaceutical products, which notice reflects approval by the agency of manufacture, use of sale for human administration. The pack or kit can be labeled with information regarding mode of administration, sequence of administration (e.g., separately, sequentially or concurrently), or the like. The pack or kit may also include means for reminding the patient to take the therapy. The pack or kit can be a single unit dosage of the combination therapy or it can be a plurality of unit dosages. In particular, the agents can be separated, mixed together in any combination, present in a formulation or tablet.

The preferred embodiments provide compositions and methods to promote urinary bladder health. All preferred embodiments provide varying amounts of thymoquinone or a SFE of *Nigella sativa* containing 2.0 to 6.0% (w/w) thymoquinone. Generally the formulations comprise a thymoquinone formulation containing 2.0 to 6.0% (w/w) thymoquinone prepared by supercritical fluid extraction of *Nigella sativa* seeds and at least one member selected from the group comprising cranberry fruit or cranberry extract and methionine. In one embodiment, the composition comprises (a) 2 mg/kg of a thymoquinone formulation containing 2.0 to 6.0% (w/w) thymoquinone; (b) 20 mg/kg cranberry extract; and (c) 40 mg/kg methionine.

EXAMPLES

Example 1

Thymoquinone Inhibits Inflammation-Stimulated Nitric Oxide Biosynthesis in Myocytes Objective—The objective of this experiment was to determine if thymoquinone could inhibit the inflammatory response of myocytes as measured by the inhibition of iNOS biosynthesis of NO.

The Model—The C2C12 murine myocyte model was used in this Example. This model was selected to serve as the surrogate for muscle cells of the bladder that are exposed to the inflammatory stimuli of the invading bacteria, modeled by lipopolysaccharide (LPS), as well as the counter-inflammatory responses of the bladder infiltrating macrophage, modeled by interferon gamma (IFγ) and tumor necrosis factor alpha (TNFα). Alterations in NO levels have been demonstrated in some humans with interstitial cystitis as well as in chemically induced animal models of cystitis. A significant increase in baseline NO production in cats with feline interstitial cystitis compared with that in healthy cats has been found in smooth muscle and mucosal strips.

Chemicals—Heat-inactivated fetal bovine serum (HIFBS), penicillin and streptomycin solution, and Dulbecco's Modification of Eagle's Medium (DMEM) were purchased from Mediatech (Herndon, Va.). 2-N-7-(nitrobenz-2-oxa-1,3-diazol-4-yl)amino-2-deoxy-d-glucose (2-NBDG) and N-methyl-4-hydrazino-7-nitrobenzofurazan (NBDM) were obtained from Invitrogen (Carlsbad, Calif.). Thymoquinone, bacterial lipopolysaccharide (LPS), murine TNFα and Interferon-γ and all standard chemicals, unless noted, were obtained from Sigma (St Louis, Mo.) and were of the highest purity commercially available.

Cell culture and treatment—Mouse C2C12 myoblasts (American Type Culture Collection, Manassas, Va.) were maintained in Dulbecco's modified Eagle's medium (DMEM) supplemented with 10% fetal calf serum (FCS), 50 units/ml penicillin and 50 µg/ml streptomycin. As cells reached confluence, the medium was switched to the differentiation medium containing DMEM and 2% horse serum. Medium was changed every other day. After 4 additional days, the differentiated C2C12 cells had fused into myotubes, which were then treated in serum-free DMEM with either vehicle alone (0.1% DMSO), or 50, 10, 5, or 1 µg thymoquinone/mL for 1 hour and then stimulated with a cytokine mixture containing 1 µg LPS/mL, 50 ng TNFα/mL and 100 U IFγ/mL (LTI) for 20 hours. At the end of the treatment period, media were sampled for determination of NO.

Nitric oxide determination—NBD methylhydrazine (NBDM, N-methyl-4-hydrazino-7-nitrobenzofurazan) was used to detect N-methyl-4-amino-7-nitrobenzofuazan, the fluorescent product of the NBDM reagent with nitrite (Buldt A, Karst U. Determination of nitrite in waters by microplate fluorescence spectroscopy and HPLC with fluorescence detection. *Anal Chem.* Aug. 1, 1999; 71(15):3003-3007). In a separate, black-walled, 96-well, microtiter plate, a 7 µL aliquot of a $4.8 \times 10^{-4}$ mol NBDM/L solution was added to 200 µL of the supernatant media followed by the addition of 15 µL of concentrated phosphoric acid. After a reaction time of 30 minutes at ambient temperature, the fluorescence was read with 485 nm excitation filter and a 530 nm emission filter in a Packard Fluorocount spectrofluorometer (Model#BF10000, Meridan, Conn.). Fluoresence was linear in the range of $3.59 \times 10^{-7}$ to $1.44 \times 10^{-5}$ mol nitrite/L. The standard deviation was 3.5 percent for $1.44 \times 10^{-6}$ mol nitrite/L. Experiments were performed a minimum of three times with eight replicates per dose, capturing the median inhibitory concentration ($IC_{50}$) when possible.

Calculations—The median inhibitory concentrations ($IC_{50}$) and 95% confidence interval were calculated using CalcuSyn (BIOSOFT, Ferguson, Mo.). This statistical package performs multiple drug dose-effect calculations using the Median Effect methods described by Chou and Talalay [Chou T C, Talalay P. Quantitative analysis of dose-effect relationships: the combined effects of multiple drugs or enzyme inhibitors. *Adv Enzyme Regul.* 1984; 22:27-55].

Results—Unexpectedly, thymoquinone was a potent inhibitor of iNOS-mediated NO production in myocytes stimulated with the trivalent cytokine mixture and exhibited a median inhibitory concentration of 1.6 µg thymoquinone/mL with a 95% confidence interval of 1.1 to 2.3 µg/mL. While thymoquinone has been demonstrated to be similarly effective in inhibiting NO production in LPS-stimulated macrophages ($IC_{50}$=1.4-2.8 µg/mL), this effect was limited to a single stimulating agent LPS in macrophages [El-Mahmoudy A, Matsuyama H, Borgan M A, et al. Thymoquinone suppresses expression of inducible nitric oxide synthase in rat macrophages. *Int Immunopharmacol.* October 2002; 2(11):1603-1611]. As myocytes and macrophages are distinct cell types and the trivalent, pro-inflammatory cocktail used in this example differs from the single, LPS stimulation previously used, these results are unexpected and serve to demonstrate the potential for the use of thymoquine in formulations designed to treat cystitis.

Thus, the inhibitory effect of thymoquinone in this example demonstrates a novel result encompassing multiple receptor signaling pathways in the myocytes. Such a finding has thus far not been reported and reveals the potential usefulness for thymoquinone for use in the treatment of urinary cystitis alone or in combination with other agents.

Example 2

Select Supercritical Fluid Extracts of *Nigella sativia* Containing Thymoquinone Inhibit Inflammation-Stimulated Nitric Oxide Biosynthesis in Myocytes More Effectively Than Pure Thymoquinone Alone Objective—The objective of this experiment was to determine whether supercritical fluid extracts of *N. sativa* containing thymoquinone can directly reduce inflammation-induced NO secretion in myocytes more effectively than pure thymoquinone alone.

The Model—The C2C12 murine myocyte model as described in Example 1 was used.

Chemicals—all chemicals were obtained from sources as described in Example 1 and were of the highest purity commercially available.

Raw material purchase—The black seeds of *N. sativa* are seasonal, available from April to June of every year. The main source is in northern parts of India particularly in Uttar Pradesh. Stocked material is available through out the year. The cost generally fluctuates between $2.5/kg to $5.0/kg.

Grinding and sieving—Once the material is purchased it is ground to a fine powder between 20-30 mesh. A magnetic system ensures removal of metallic impurities, particularly iron.

Figure 2:
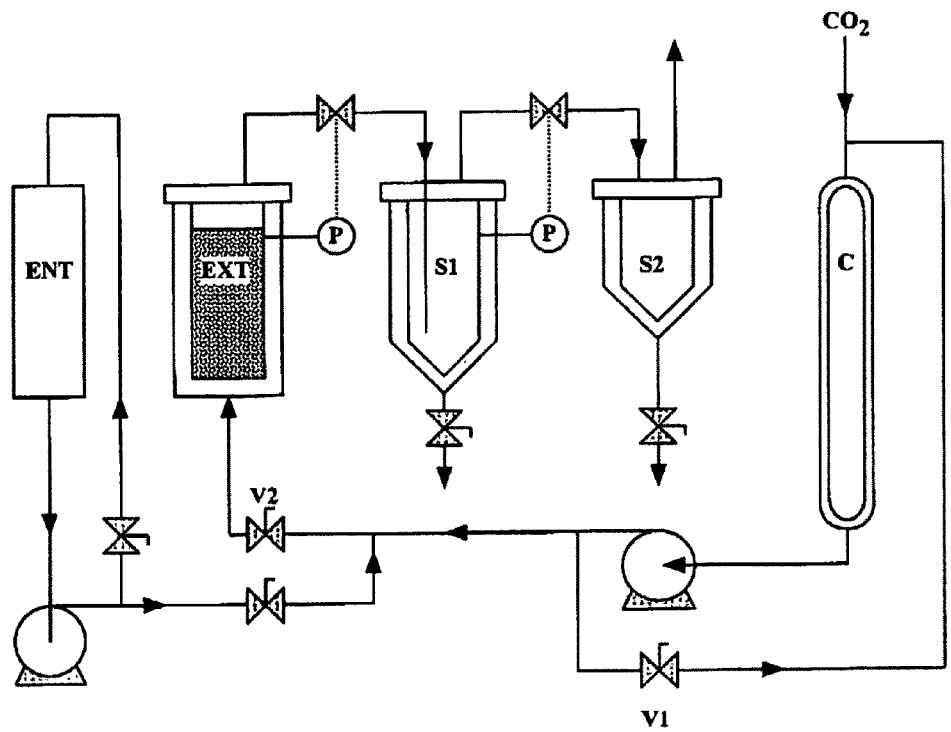
FIG. 2 is a schematic presentation of the setup for supercritical fluid extraction.

Supercritical Fluid Extraction—In this example, the process conditions during the extraction of *N. salivia* seeds with supercritical carbon dioxide extraction were varied with respect to pressure, temperature and time (Table 2). The extraction was performed in a polyvalent pilot plant extraction set-up shown schematically in FIG. 2. Liquid carbon dioxide entering the apparatus is cooled in condensor C before it is pressurized and passed into the system. The flow rate was adjusted manually before the experiment. The temperatures of the extractor, carbon dioxide, and separators 1 and 2 (S1/S2) were automatically regulated through the recirculation of thermostated water from three individually regulated water baths.

The ground *N. sativa* seeds were loaded into a cylindrical container that was equipped with steel mesh filters on both ends, thus enabling carbon dioxide to pass the cylinder without transport of solids to the exterior. After prepressurization of the total system and the regulation of the carbon dioxide flow rate, the extractor (EXT) was depressurized and the cylinder was subsequently placed inside the extractor, after which the complete carbon dioxide flow was redirected toward the extractor using valves V1 and V2. The temperature/pressure combinations of both separator vessels S1 and S2 were controlled individually. The extraction was stopped by redirecting the carbon dioxide flow again to recirculation over the condenser. The solid residue was removed from the extractor after stepwise depressurization of the entire system. Subsequently, both separator vessels were rinsed with hexane, and extracts were collected in UV-opaque bottles to prevent UV-activated degradation of the extract. Pressure/temperature combinations and extraction times for the seven extracts obtained (TQ1-TQ7) are presented in Table 2.

Thymoquinone concentration—Thymoquinone content of the various fractions obtained were determined by HPLC analysis as described by Ghosheh (Ghosheh O A, Houdi A A, Crooks P A. High performance liquid chromatographic analysis of the pharmacologically active quinones and related compounds in the oil of the black seed (*Nigella sativa* L.). *J Pharm Biomed Anal*. April 1999; 19(5):757-762) with no modfications.

Cell culture and treatment—Mouse C2C12 myoblasts (American Type Culture Collection, Manassas, Va.) were maintained in Dulbecco's modified Eagle's medium (DMEM) supplemented with 10% fetal calf serum (FCS), 50 units/mL penicillin and 50 µg/ml streptomycin. As cells reached confluence, the medium was switched to the differentiation medium containing DMEM and 2% horse serum. Medium was changed every other day. After 4 additional days, the differentiated C2C12 cells had fused into myotubes, which were then treated in serum-free DMEM with either vehicle alone (0.1% DMSO), or 50, 10, 5, or 1 µg/mL of the thymoquinone test formulation for 1 hour and then stimulated with a cytokine mixture containing 1 µg LPS/mL, 50 ng TNFα/mL and 100 U IFγ/mL for 20 hours. At the end of the treatment period, media were sampled for determination of NO.

Nitric oxide determination—NO production from stimulated myocytes was performed as described in Example 1. Experiments were performed a minimum of two times with eight replicates per dose, capturing the median inhibitory concentration ($IC_{50}$) when possible.

Calculations—The median inhibitory concentrations ($IC_{50}$) and 95% confidence interval were calculated as outlined in Example 1.

Results—The highest thymoquinone concentrations of 6.80 and 5.98%, respectively, were found in TQ2 and TQ3 extracted at 120-130 Bar at 40° C. for 4 and 6 hours (Table 2). Of these two extracts, however, only TQ3 exhibited anti-inflammatory activity in excess of its thymoquinone content (Table 3). TQ3 exhibited an $IC_{50}$ of 0.87 µg thymoquinone/mL, significantly ($p<0.05$) lower than the $IC_{50}$ of pure thymoquinone. It appears that the additional 2 hours of extraction at 120-130 Bar and 40° C. produced a unique combination of anti-inflammatory phytochemicals. Extraction of *N. sativa* seeds at 120-130 for only 2 (TQ1) or 4 (TQ2) hours resulted in anti-inflammatory formulations with efficacy in concert with their thymoquinone content (Table 3).

Similarly, increasing the pressure to 160-180 Bar and maintaining the temperature at 40° C. for 2 hours resulted in an extract (TQ4) with anti-inflammatory activity, on a weight basis, similar to thymoquinone. Increasing the temperature to 60° C., while maintaining the pressure at 160-180 Bar and time to 2 hours, once again produced an extract (TQ5) with anti-inflammatory activity unexpectedly greater than that of pure thymoquinone (Table 3).

A third extract TQ6 was produced with anti-inflammatory activity greater than its thymoquinone content by extracting for 10 hours with a pressure of 200 Bar and a temperature of 50° C. (Table 3). While TQ6 contained only 2.02% thymoquinone, The $IC_{50}$ of this formulation was the lowest in the series of seven extracts, 0.59 µg thymoquinone/mL, indicating the unexpected, positive interaction of extracted, anti-inflammatory phytochemicals. Further increasing the pressure and temperature to 300 Bar and 60° C., while extracting for 3 hours resulted in a low total thymoquinone concentration of 0.98% and anti-inflammatory activity consistent with the thymoquinone content, $IC_{50}=1.4$ µg thymoquinone/mL.

Optimal supercritical carbon dioxide extraction conditions for iNOS inhibition in myocytes by *N. sativa* seed extracts were: (a) a six-hour extraction period at 120-130 Bar and 40° C.; (b) a two-hour extraction period at 160-180 Bar and 60° C.; or (c) a 10-hour extraction period at 200 Bar and 50° C. These extraction conditions resulted in *N. sativa* black seed extracts containing 2 to 6% thymoquinone and having inhibitor activity unexpectedly in excess of their thymoquinone content.

TABLE 2

Thymoquinone content of supercritical carbon dioxide extracts of *N. sativa* seeds under various extraction conditions of pressure, temperature and extraction time.

| | Process conditions | | | |
| --- | --- | --- | --- | --- |
| Sample | Pressure (Bar) | Temperature (° C.) | Time (h) | Thymoquinone (% w/w) |
| TQ Sigma | — | — | — | 100 |
| TQ1 | 120-130 | 40 | 2 | 4.42 |
| TQ2 | 120-130 | 40 | 4 | 6.80 |

TABLE 2-continued

Thymoquinone content of supercritical carbon dioxide extracts of N. sativa seeds under various extraction conditions of pressure, temperature and extraction time.

| Sample | Process conditions | | | Thymoquinone (% w/w) |
|---|---|---|---|---|
| | Pressure (Bar) | Temperature (°C.) | Time (h) | |
| TQ3 | 120-130 | 40 | 6 | 5.98 |
| TQ4 | 160-180 | 40 | 2 | 4.41 |
| TQ5 | 160-180 | 60 | 2 | 2.95 |
| TQ6 | 200 | 50 | 10 | 2.02 |
| TQ7 | 300 | 60 | 3 | 0.98 |

TABLE 3

Median inhibitory concentrations for iNOS biosynthesis of NO of various supercritical fluid extracts of N. sativa seed extracts are out of proportion to thymoquinone content.

| Sample | Thymoquinone (% w/w) | Adjusted iNOS† ($IC_{50}$) (μg/mL) |
|---|---|---|
| TQ Sigma | 100 | 1.6 (1.1-2.3)†† |
| TQ1 | 4.42 | 2.4 |
| TQ2 | 6.80 | 1.5 |
| TQ3 | 5.98 | 0.87* |
| TQ4 | 4.41 | 2.3 |
| TQ5 | 2.95 | 0.92* |
| TQ6 | 2.02 | 0.59* |
| TQ7 | 0.98 | 1.4 |

†Inhibition of LTI-stimulated iNOS biosynthesais of NO in C2C12 myocytes adjusted for thymoquinone content.
††95% confidence interval for the $IC_{50}$ of TQSigma = 1.1-2.3.
*Significantly less (p < 0.05) than TQSigma.

Example 3

Screening Additional N. sativa Phytochemicals for Anti-Inflammatory Activity

In order to identify the other anti-inflammatory phytochemicals potentially extracted pure anethole, thymol, carvacrol and cymene were purchased from Sigma and tested in LTI-stimulated, C2C12 myocytes as described in Example 1. None of these pure compounds resulted in median inhibitory concentrations less than 10 μg/mL and were not considered likely contributors to the increased effectiveness of the extracts in Example 2 without unexpected synergy.

Example 4

Composition of a Dietary Supplement for Urinary Health

The most preferred composition of the dietary supplement, in capsule form, would supply the following amounts of active ingredients per kg body weight per day: (a) 2 mg/kg of a thymoquinone formulation containing 2.0 to 6.0% (w/w) thymoquinone; (b) 20 mg/kg cranberry extract; and (c) 40 mg/kg methionine. Such a formulation would provide the most rapid acidification of the urine as well as potent anti-inflammatory activity. However, palatability of methionine may be a factor in some animals and in such instances, the methionine component may be eliminated as the cranberry extract also serves to acidify the urine.

Improvement in clinical signs due to cystitis or urinary tract infection would be expected to occur following two to five doses. Additionally, the formulation may be used to support or normalize urinary tract health. This result would be expected in all mammals affected by cystitis or urinary tract infections.

Thus, the present invention provides a dietary supplement comprising a thymoquinone formulation containing 0.90 to 7.0 (% w/w) thymoquinone and at least one member selected from the group consisting of cranberry fruit extract and methionine. It will be readily apparent to those skilled in the art that various changes and modifications of an obvious nature may be made without departing from the spirit of the invention, and all such changes and modifications are considered to fall within the scope of the invention as defined by the appended claims. Such changes and modifications would include, but not be limited to, the incipient ingredients added to affect the capsule, tablet, capsule, lotion, spray or bar manufacturing process as well as the addition of vitamins, nutrients and other herbs.

The invention claimed is:

1. A method of treating inflammation associated with idiopathic cystitis in animals which comprises administering to an animal suffering signs or symptoms of idiopathic cystitis a composition comprising effective amounts of a thymoquinine-enriched oil extract fraction from the ground seeds of Nigella sativa and at least one component selected from the group consisting of cranberry fruit, cranberry extract, cranberry juice, and methionine, whereby the oil extract fraction is obtained by:
    (a) extracting the ground Nigella sativa seeds with supercritical carbon dioxide at 120-130 bar at 40° C. for 6 hours to obtain a fraction and collecting the fraction;
    (b) extracting the ground Nigella sativa seeds with supercritical carbon dioxide at 160-190 bar at 60° C. for 2 hours to obtain a fraction and collecting the fraction; or
    (c) extracting the ground Nigella sativa seeds with supercritical carbon dioxide at 200 bar at 50° C. for 10 hours to obtain a fraction and collecting the fraction; and continuing administration until said signs or symptoms are reduced or eliminated.

2. The method of claim 1 wherein the animal is a mammal selected from the group consisting of humans, nonhuman primates, dogs, cats, horses or cattle.

3. The method of claim 1 wherein the administration is oral.

4. The method of claim 1, wherein the administration is by injection.

* * * * *